United States Patent
Kai et al.

(10) Patent No.: US 11,320,430 B2
(45) Date of Patent: May 3, 2022

(54) MAGNETIC PARTICLE DISPERSION

(71) Applicants: JSR CORPORATION, Minato-ku (JP); JSR LIFE SCIENCES CORPORATION, Minato-ku (JP); JSR Life Sciences, LLC, Sunnyvale, CA (US); JSR Micro N.V., Leuven (BE)

(72) Inventors: Hirokazu Kai, Minato-ku (JP); Kousuke Hiroki, Minato-ku (JP); Yuuichi Ueya, Minato-ku (JP)

(73) Assignees: JSR CORPORATION, Minato-ku (JP); JSR LIFE SCIENCES CORPORATION, Minato-ku (JP); JSR Life Sciences, LLC, Sunnyvale, CA (US); JSR Micro N.V., Leuven (BE)

( * ) Notice: Subject to any disclaimer, the term of this patent is extended or adjusted under 35 U.S.C. 154(b) by 0 days.

(21) Appl. No.: 16/348,996

(22) PCT Filed: Dec. 27, 2017

(86) PCT No.: PCT/JP2017/046926
§ 371 (c)(1),
(2) Date: May 10, 2019

(87) PCT Pub. No.: WO2018/124185
PCT Pub. Date: Jul. 5, 2018

(65) Prior Publication Data
US 2019/0271696 A1    Sep. 5, 2019

(30) Foreign Application Priority Data

Dec. 28, 2016 (JP) .............................. JP2016-255830

(51) Int. Cl.
| | | |
|---|---|---|
| *G01N 33/553* | (2006.01) | |
| *C07D 275/03* | (2006.01) | |
| *C07D 275/04* | (2006.01) | |
| *C07D 275/02* | (2006.01) | |

(52) U.S. Cl.
CPC ......... *G01N 33/553* (2013.01); *C07D 275/02* (2013.01); *C07D 275/03* (2013.01); *C07D 275/04* (2013.01)

(58) Field of Classification Search
CPC ........... G01N 33/553; G01N 33/54333; G01N 2446/00; C07D 275/03; C07D 275/04; C07D 275/02
See application file for complete search history.

(56) References Cited

U.S. PATENT DOCUMENTS

| | | | |
|---|---|---|---|
| 9,702,869 | B2 | 7/2017 | Hu et al. |
| 2012/0021944 | A1 | 1/2012 | Baker et al. |
| 2014/0024556 | A1 | 1/2014 | Baker et al. |
| 2014/0051070 | A1 | 2/2014 | Arai et al. |
| 2014/0147935 | A1 | 5/2014 | Imus et al. |
| 2015/0079612 | A1 | 3/2015 | Hu et al. |

FOREIGN PATENT DOCUMENTS

| | | |
|---|---|---|
| CN | 102565405 A | 7/2012 |
| EP | 2 208 531 A1 | 7/2010 |
| JP | 57-24369 A | 2/1982 |
| JP | 61-215602 A | 9/1986 |
| JP | 61-215603 A | 9/1986 |
| JP | 61-215604 A | 9/1986 |
| JP | 11-326331 A | 11/1999 |
| JP | 2006-226690 A | 8/2006 |
| JP | 2008-32411 A | 2/2008 |
| JP | 4716034 B2 | 7/2011 |
| JP | 2013-532821 A | 8/2013 |
| JP | 2014-501392 A | 1/2014 |
| JP | 2015-502356 A | 1/2015 |
| JP | 2016-200598 A | 12/2016 |
| WO | WO 2012/054638 A2 | 4/2012 |
| WO | WO 2012/111685 A1 | 8/2012 |
| WO | WO 2012/111687 A1 | 8/2012 |
| WO | WO 2016/043291 A1 | 3/2016 |

OTHER PUBLICATIONS

Roche. mRNA isolation kit. Cat. No. 11741985001. www.roche-applied-science.com. Roche Diagnostics GmbH, Germany, Version 08, 2009, pp. 1-20 (Year: 2009).*
Gasso et al. Magnetic bead coatings: today and tomorrow. Sepmag.eu. Edited by Dr. Sergi Gasso & Dr. Lluis M. Martinez., Posted on Dec. 12, 2014, SEPMAG Systems, Barcelona. pp. 1-21 (Year: 2014).*
Office Action dated Feb. 16, 2021 in corresponding European Patent Application No. 17 887 925.0, 7 pages.
Extended European Search Repon dated Jul. 3, 2020 in Patent Application No. 17887925.0, 9 pages.
"Proclin(TM) 300 Presentative for Diagnostic Reagents" Sigma Aldrich, XP055705320, 2015, 2 pages.
"PolyLink Protein Coupling Kit for COOH Microspheres" Polysciences Inc., XP055705325, 2013, 2 pages.
"Magnosphere(TM) MS300/Carboxyl" JSR Corporation, XP055705327, Oct. 17, 2016, 2 pages.
International Search Report and Written Opinion dated Apr. 3, 2018 in PCT/JP2017/046926, 16 pages (with English translation).
Office Action dated Jun. 20, 2017 in Japanese Patent Application No. 2016-255830, 9 pages (with English translation).

(Continued)

*Primary Examiner* — Shafiqul Haq

(74) *Attorney, Agent, or Firm* — Oblon, McClelland, Maier & Neustadt, L.L.P.

(57) ABSTRACT

The present invention relates to a magnetic particle dispersion, and the magnetic particle dispersion includes a magnetic particle, an isothiazoline compound, and an aqueous medium.

5 Claims, No Drawings

(56) References Cited

OTHER PUBLICATIONS

"Anti-HA-tag mAb-Magnetic Beads" Medical & Biological Laboratories Co., Ltd., http://ruc.mbl.co.jp/bic/dtl/dtifiled/M180-11-v2.pdf, 5 pages.
"ProClin Product Information Page" Sigma-Aldrich Japan K.K., http://www.sigmaaldrich.com/japan/safc/proclin.html, 5 pages (with English translation provided from Google on Jul. 11, 2019).

* cited by examiner

MAGNETIC PARTICLE DISPERSION

TECHNICAL FIELD

The present invention relates to a magnetic particle dispersion.

BACKGROUND ART

In recent years, magnetic particles have been increasingly actively applied particularly to biochemical applications such as diagnostic agents and research of pharmaceutical products because magnetic particles are easily washed by magnetic separation and can provide excellent reaction fields for immunoreactions between antigens and antibodies, hybridization between DNAs or between DNA and RNA, and interaction between candidate substances of pharmaceutical products and substances in a body, for example.

The magnetic particles are usually stored and used in the form of magnetic particle dispersions. For example, in the biochemical applications, magnetic particle dispersions are produced in advance or commercially available magnetic particle dispersions are purchased in advance and then used at the required timing, and therefore the dispersions may be stored for a long period from production or purchase to usage in some cases. In particular, commercially available products may be stored for a long period for the purpose of storage and/or transport. Accordingly, the dispersions are demanded to have storage stability.

Magnetic particle dispersions for use in, for example, biochemical applications are usually aqueous dispersions and therefore may be compounded with preservative agents. Such a preservative agent conventionally used has been sodium azide (Patent Literature 1).

CITATION LIST

Patent Literature

Patent Literature 1: WO 2012/111687

SUMMARY OF INVENTION

Technical Problem

However, it has been found that a magnetic particle dispersion containing sodium azide easily causes the function of a magnetic particle by itself to be deteriorated, while being excellent in preservative effect.

One embodiment of the present invention provides a magnetic particle dispersion that can be suppressed in deterioration in the function of a magnetic particle by itself and that is excellent in storage stability.

Solution to Problem

The present inventors have made intensive studies in order to solve the above problem, and as a result, have found that the problem can be solved by the following magnetic particle dispersion, thereby leading to completion of the present invention.

Configuration examples of the present invention are as follows.

<1> A magnetic particle dispersion including a magnetic particle, an isothiazoline compound, and an aqueous medium.

<2> The dispersion according to <1>, containing 0.001 to 10 parts by mass of the isothiazoline compound based on 100 parts by mass of the magnetic particle.

<3> The dispersion according to <1> or <2>, wherein the isothiazoline compound is at least one selected from the group consisting of a compound represented by formula (1) and a compound represented by formula (2).

[Formula 1]

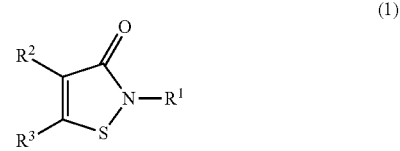

(1)

In formula (1), $R^1$ represents a hydrogen atom, or a substituted or unsubstituted hydrocarbon group, and $R^2$ and $R^3$ each independently represent a hydrogen atom, a halogen atom, or an organic group, provided that $R^2$ and $R^3$ are optionally bound to each other to form a ring other than a benzene ring.

[Formula 2]

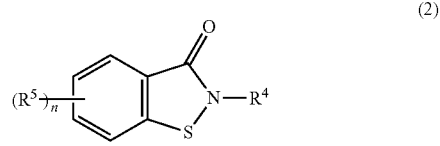

(2)

In formula (2), $R^4$ represents a hydrogen atom, or a substituted or unsubstituted hydrocarbon group, $R^5$ independently represents a hydrogen atom, a halogen atom, or an organic group, and n represents an integer of 0 to 4.

<4> The dispersion according to any of <1> to <3>, wherein the magnetic particle has a polymer layer, a polar group, or a ligand.

<5> The dispersion according to <4>, wherein the content of the polar group and the ligand in the magnetic particle is 0.1 to 100 μmol/g.

<6> The dispersion according to <4> or <5>, wherein a parking area of the polar group and the ligand in the magnetic particle is 2.5 (Å$^2$/polar group and ligand) or more.

<7> The dispersion according to any of <1> to <6>, wherein the magnetic particle has a structure that can be hydrolyzed.

<8> The dispersion according to any of <1> to <7>, wherein the magnetic particle is a magnetic particle having an ester bond-containing polymer layer, a magnetic particle having at least one polar group selected from the group consisting of an amino group, an aldehyde group, a carboxyl group, a tosyl group, a mercapto group, a hydroxyl group, an epoxy group, and an ester group, a magnetic particle where a ligand is bound via an ester bond, or a magnetic particle where a cyclic amide bond-containing or ester bond-containing ligand is bound.

<9> The dispersion according to any of <1> to <8>, wherein a volume average particle size of the magnetic particle is 0.1 to 10 μm.

Advantageous Effects of Invention

According to one embodiment of the present invention, there can be easily obtained a magnetic particle dispersion that can be suppressed in deterioration in the function of a magnetic particle by itself and that is excellent in storage stability, and also a magnetic particle dispersion that not only is suppressed in deterioration in the function of a magnetic particle by itself, but also is excellent in preservative/bactericidal effect.

Accordingly, one embodiment of the present invention can allow the function of a magnetic particle to be maintained over a long period, and therefore can attain a desired result, for example, can be suppressed in reduction of the sensitizing doses of an antigen and an antibody and can allow a high detection sensitivity to be maintained even when a magnetic particle dispersion stored for a long period is used. Therefore, a magnetic particle dispersion according to one embodiment of the present invention can be suitably used in biochemical applications, for example.

DESCRIPTION OF EMBODIMENTS

Hereinafter, suitable embodiments according to the present invention will be described in detail. It is to be understood that the present invention is not limited to only embodiments described below and encompasses various modifications carried out without departing from the gist of the present invention. Herein, the expression "A to B" representing a numerical value range is used synonymously with the expression "A or more and B or less", and the numerical value range includes A and B. Herein, the term "X (meth)acrylate" is a concept including both "X acrylate" and "X methacrylate".

<<Magnetic Particle Dispersion>>

A magnetic particle dispersion according to one embodiment of the present invention (hereinafter, also referred to as "present dispersion") includes a magnetic particle, an isothiazoline compound, and an aqueous medium.

While the reason why at least one of the above effects is exerted by the present dispersion is not necessarily clear, the reason is considered because the isothiazoline compound can cover the magnetic particle surface or can adsorb to the magnetic particle surface, to allow the magnetic particle surface to be in a hydrophobic atmosphere, thereby not only suppressing deterioration in the function of the magnetic particle by itself, but also providing a magnetic particle dispersion excellent in storage stability due to the preservative/bactericidal effect exerted by the isothiazoline compound by itself.

More specific one reason why the above effects are exerted by the present dispersion is also considered as follows.

A magnetic particle suitable for biochemical applications such as immunodiagnosis preferably has a polymer layer on the surface thereof. While such a polymer layer to be used is a layer having a water-insoluble and hydrophobic surface, impurities are easily attached onto the surface. Since impurities may be detected as noises, for example, in immunodiagnosis, there is performed, for example, a treatment where a particle surface is subjected to a hydrophilization treatment, thereby suppressing attachment of impurities and reducing noises. However, it has been found that a case where a magnetic particle is subjected to the hydrophilization treatment and in particular an alkaline compound such as sodium azide is present in a magnetic particle dispersion is problematic in terms of, for example, a reduction in the sensitizing dose of, for example, an antibody because a polymer on the particle surface subjected to the hydrophilization treatment easily undergoes hydrolysis to cause a ligand and/or a polar group for immobilizing such a ligand to be detached from the particle surface, resulting in deterioration in the function of a magnetic particle by itself. On the other hand, it is considered that an isothiazoline compound can be added to a magnetic particle dispersion as in one embodiment of the present invention, thereby covering a magnetic particle surface or adsorbing to a magnetic particle surface to allow the particle surface to be in a hydrophobic atmosphere. It is presumed that the isothiazoline compound is relatively high in hydrophobicity and thus the isothiazoline compound is retained on the magnetic particle to enable water absorbability of a polymer layer on the magnetic particle surface to be decreased, resulting in suppression of swelling due to hydration and reduction in, for example, hydrolysis of a ligand and/or a polar group for immobilizing such a ligand by an alkali, while a particle surface high in hydrophilicity causes progression of hydrolysis under a basic condition and causes hydrolysis of an ester bond after a lapse of time.

<Magnetic Particle>

The magnetic particle is not particularly limited as long as the magnetic particle is a particle including a material that can be easily magnetized by magnetic induction, and a conventionally known particle can be used therefor. The magnetic particle is preferably a particle having a polymer (resin) layer, a polar group, or a ligand from the viewpoint that, for example, at least one of the effects of the present invention can be more exerted, and is preferably an insoluble magnetic particle that is stable in an aqueous medium.

The magnetic particle may be used singly or two or more kinds.

The magnetic particle is preferably a particle in which a material that can be easily magnetized by magnetic induction is contained in a resin from the viewpoint of, for example, suitable usability in biochemical applications and ease of separation and washing.

The material that can be easily magnetized by magnetic induction is not particularly limited, and examples include ferrosoferric oxide ($Fe_3O_4$), iron sesquioxide ($\gamma$-$Fe_2O_3$), various ferrites, metals such as iron, manganese, nickel, cobalt and chromium, and alloys of cobalt, nickel, and manganese, for example.

In particular, a superparamagnetic fine particle including iron oxides, having a particle size of 50 nm or less, preferably 30 nm or less, and preferably having a particle size of 5 nm or more, is preferable, a superparamagnetic fine particle including ferrite represented by $AFe_2O_4$ (A represents, for example, Mn, Co, Ni, Mg, Cu, Zn, or $Li_{0.5}Fe_{0.5}$), magnetite ($Fe_3O_4$), or $\gamma$-$Fe_2O_3$ is more preferable, and a superparamagnetic fine particle made of $\gamma$-$Fe_2O_3$ and $Fe_3O_4$ is particularly preferable from the viewpoint of, for example, strong saturation magnetization and less residual magnetization.

The polymer layer may be a hydrophilic polymer layer or a hydrophobic polymer layer and is not particularly limited. A magnetic particle having a polymer layer derived from at least one selected from the group consisting of an aromatic vinyl monomer and an ethylenically unsaturated carboxylic acid is preferable, a magnetic particle having an ester bond-containing polymer layer is more preferable, and a magnetic particle having the following first polymer layer is further preferable, from the viewpoint that, for example, a magnetic particle dispersion more excellent in magnetic particle dispersibility and storage stability can be easily obtained.

The magnetic particle having a polar group is not particularly limited, and is preferably a magnetic particle that can carry a ligand such as an antigen or an antibody, via the polar group, more preferably a magnetic particle having at least one polar group selected from the group consisting of an amino group, an aldehyde group, a carboxyl group, a tosyl group, a mercapto group, a hydroxyl group, and an epoxy group, for example.

The polar group is usually formed on the polymer layer.

The magnetic particle having a ligand may be appropriately selected depending on the desired use, and is preferably a magnetic particle having a ligand that can be bound specifically to a measurement object, more preferably a magnetic particle having, for example, protein such as protein A, protein G, protein L, streptavidin, avidin, an antigen, an antibody, or an enzyme, nucleic acid such as DNA or RNA, a low-molecular pharmaceutical product, a physiologically active substance, and a low-molecular compound such as oligopeptide, oligonucleotide, or a lipid.

The ligand is usually carried via the polar group.

In particular, the magnetic particle having a polar group or a structure that can be hydrolyzed is preferable from the viewpoint that, for example, the effects of the present invention can be more exerted.

Examples of the structure that can be hydrolyzed include an ester bond contained in the polymer layer, an ester bond for binding a ligand, and a cyclic amide or an ester bond contained in a ligand.

The magnetic particle having a polar group or a structure that can be hydrolyzed is suitably used in, for example, biochemical applications, but such a group is, for example, decomposed in an aqueous medium, and easily causes deterioration in the function of the magnetic particle by itself in the case where the magnetic particle is stored in an aqueous medium. The present inventors have made intensive studies, and as a result, have found that an isothiazoline compound can be used to thereby suppress such deterioration in the function of the magnetic particle by itself even in use of the magnetic particle having a polar group or a structure that can be hydrolyzed. Therefore, the magnetic particle having a polar group or a structure that can be hydrolyzed is preferably used in one embodiment of the present invention in that the magnetic particle can be suitably used in, for example, biochemical applications.

Examples of the magnetic particle suitably include a magnetic particle which has a first polymer layer having hydrophobicity on the surface of a mother particle including the superparamagnetic fine particle and which has a second polymer layer having a glycidyl group on at least the surface thereof, on the first polymer layer, the glycidyl group being chemically modified to thereby introduce a polar group including one or more atoms of at least one kind of atom selected from the group consisting of an oxygen atom, a nitrogen atom, and a sulfur atom, described in JP-A-2008-32411.

Examples of the mother particle include (I) a particle in which the superparamagnetic fine particle is dispersed in a continuous phase of a non-magnetic material such as an organic polymer, (II) a particle with a secondary aggregate of the superparamagnetic fine particle as a core, and a non-magnetic material such as an organic polymer as a shell, and (III) a particle including a nuclear particle including a non-magnetic material such as an organic polymer, and a secondary aggregate layer (magnetic material layer) of the superparamagnetic fine particle, provided on the surface of the nuclear particle. In particular, the mother particle (III) is preferable from the viewpoint that, for example, excellent magnetic responsiveness is imparted and the particle size can be uniformly controlled.

The nuclear particle is basically a non-magnetic substance, any of an organic substance and an inorganic substance can be used and can be appropriately selected depending on the intended use of the present dispersion, for example, and the nuclear particle is preferably an organic substance such as a polymer from the viewpoint of processability in formation of the mother particle and lightweight. Representative examples of the organic substance can include a polymer. Such a polymer is particularly preferably a vinyl polymer, most preferably crosslinked polystyrene or crosslinked polymethyl methacrylate. Such a polymer may have a functional group introduced, such as a carboxyl group.

Such a nuclear particle can be produced by a conventionally known method, for example, any method described in JP-B-1982-24369, JP-A-1986-215602, JP-A-1986-215603, and JP-A-1986-215604.

The average particle size of the nuclear particle is preferably 0.4 μm or more, further preferably 0.6 μm or more, particularly preferably 0.8 μm or more, and preferably 200 μm or less, further preferably 100 μm or less, particularly preferably 50 μm or less from the viewpoint that, for example, magnetic separability is excellent, gravitational sedimentation is hardly caused, and a uniform reaction field can be made.

The average particle size of the nuclear particle is the average of the particle sizes of 100 particles randomly selected in an electron micrograph.

A preferable method of forming the magnetic material layer including the superparamagnetic fine particle on the surface of the mother particle is a method including mixing the nuclear particle and the superparamagnetic fine particle, and allowing the superparamagnetic fine particle to physically adsorb to the surface of the nuclear particle, thereby forming the magnetic material layer.

Examples of the monomer for forming the first polymer layer having hydrophobicity include monofunctional monomers including aromatic vinyl monomers such as styrene, α-methylstyrene and halogenated styrene, and ethylenically unsaturated carboxylates such as methyl (meth)acrylate, ethyl (meth)acrylate, stearyl (meth)acrylate, cyclohexyl (meth)acrylate, isobornyl (meth)acrylate and tetrahydrofurfuryl (meth)acrylate, polyfunctional monomers such as ethylene glycol di(meth)acrylate, trimethylolpropane tri(meth)acrylate, pentaerythritol tri(meth)acrylate and dipentaerythritol hexa(meth)acrylate, conjugated diolefins such as butadiene and isoprene, and crosslinkable monomers such as divinylbenzene, diallyl phthalate and allyl (meth)acrylate.

The monomer for forming the second polymer layer is mainly for introduction of a functional group to a particle surface, and preferably contains 5% by mass or more of a glycidyl group-containing monomer based on the amount of the entire monomer. Examples of the glycidyl group-containing monomer here include glycidyl (meth)acrylate and allyl glycidyl ether.

The polar group introduced by chemically modifying the glycidyl group of the second polymer layer is preferably a ligand, for example, a functional group reactive with an antigen or an antibody, and is preferably, for example, at least one selected from an amino group, an aldehyde group, a carboxyl group, a tosyl group, a mercapto group, a hydroxyl group, an epoxy group, and an active ester group. For example, in the case where the magnetic particle has a 2,3-dihydroxypropyl group generated by hydrolysis of the polar group and the glycidyl group, the magnetic particle is favorable in bindability to a ligand such as an antigen or an antibody.

The magnetic particle, when used for immunoassay, carries a ligand that can be specifically bound to a measurement object, such as an antibody or an antigen. The magnetic particle may be a particle to which the ligand is not bound yet, or may be a particle to which the ligand is bound. The magnetic particle may be a magnetic particle, if necessary, blocked by a blocking agent such as BSA (bovine serum albumin).

For example, in the case where the measurement object is an antigen, an antibody that can be specifically bound to the antigen is carried on the magnetic particle. Such an antibody that may be used is preferably IgG (immunoglobulin G), and may be an antibody reduced in molecular weight, such as F(ab')2, Fab', and Fab. Not only IgG, but also IgM (immunoglobulin M) or a fragment reduced in molecular weight by the same treatment as in IgG may also be used. A monoclonal antibody and a polyclonal antibody can be each utilized.

Examples of a method of immobilizing a ligand to the magnetic particle include physical adsorption methods and chemically carrying methods including a covalent binding method, and an ion binding method. Examples of the physical adsorption method include a method including directly immobilizing a ligand to the magnetic particle, and a method including chemically binding a ligand to, for example, other protein such as albumin and then allowing the resultant to adsorb to the magnetic particle for immobilization.

Examples of the chemically carrying methods include a method including chemically binding a polar group such as an amino group, an aldehyde group, a carboxyl group, a tosyl group, a mercapto group, a hydroxyl group, or an epoxy group, present on the magnetic particle surface, and a ligand such as an antibody or an antigen, for direct immobilization onto the magnetic particle, a method including introducing a spacer molecule (such as a carbodiimide compound) to a space between the magnetic particle and a ligand such as an antibody or an antigen by chemical binding, for immobilization, and a method including binding a ligand such as an antibody or an antigen to, for example, other protein such as albumin, and then chemically binding the protein to the magnetic particle.

An optimal range of the content of the polar group and the ligand present on the magnetic particle varies depending on the types of the polar group and the ligand, and such a content is preferably 0.1 µmol/g or more, more preferably 1 µmol/g or more, particularly preferably 3 µmol/g or more, particularly preferably 5 µmol/g or more, and preferably 100 µmol/g or less, more preferably 60 µmol/g or less, particularly preferably 50 µmol/g or less from the viewpoint that, in general, a lower content tends to not allow any effect to be efficiently exerted and a too high content tends to cause remarkable deterioration in function due to hydrolysis.

The content of the polar group and the ligand may be measured according to a method described in Examples.

The parking area of the polar group and the ligand present on the magnetic particle is preferably 2.5 ($Å^2$/polar group and ligand) or more, more preferably about 4.2 ($Å^2$/polar group and ligand) or more, further preferably 5.0 ($Å^2$/polar group and ligand) or more. The upper limit of the parking area is preferably 100 ($Å^2$/polar group and ligand) or less, more preferably about 70 ($Å^2$/polar group and ligand) or less, further preferably 50 ($Å^2$/polar group and ligand) or less. The parking area preferably falls within the above numerical value range because the ligand can be less detached and a sufficient amount of the ligand can be maintained.

The parking area here refers to an index indicating an area occupied by one polar group or ligand on the magnetic particle surface (=surface area of magnetic particle/content of polar group and ligand). In general, the amount of the ligand bound is in reverse proportion to the numerical value of the parking area, and a larger parking area provides a smaller amount of the ligand bound.

The volume average particle size of the magnetic particle is preferably 0.1 µm or more, more preferably 0.5 µm or more, particularly preferably 1 µm or more, and preferably 20 µm or less, more preferably 15 µm or less, particularly preferably 10 µm or less from the viewpoint that, for example, a particle more excellent in dispersibility is obtained to thereby provide a dispersion more excellent in magnetic separability.

The method of measuring the average particle size of the magnetic particle is not particularly limited, and the average particle size can be measured using, for example, an electron microscope, a dynamic light scattering method, a laser diffraction method, an imaging method, and a coulter method. The average particle size in the present invention, unless particularly noted, refers to a particle size (D50) at a cumulative frequency of 50% for the number of particles which is determined when accumulated from a smaller particle size in a particle size distribution measured by use of a particle size distribution analyzer with a laser diffraction method as the measurement principle. Specifically, the average particle size is measured according to a method described in Examples below.

The content of the magnetic particle in the present dispersion is preferably 20% by mass or less, more preferably 15% by mass or less based on 100% by mass of the present dispersion from the viewpoint that, for example, a magnetic particle dispersion more excellent in magnetic separability and in storage stability for a long period can be easily obtained.

<Isothiazoline Compound>

The isothiazoline compound can be added to the present dispersion, thereby not only suppressing proliferation of bacteria and/or mold and thus generation of foreign substances, but also imparting a low toxicity to a ligand such as an enzyme or an antibody and surprisingly being capable of suppressing deterioration in the function of the magnetic particle by itself, in particular, suppressing decomposition of the polar group and the structure that can be hydrolyzed, from the magnetic particle, during storage of the present dispersion.

The isothiazoline compound may be used singly or two or more kinds.

The isothiazoline compound is not particularly limited as long as the compound is a compound having an isothiazoline backbone, and specific examples include a compound represented by the following formula (1) and a compound represented by the following formula (2). In particular, a compound having higher hydrophobicity (for example, a compound in which $R^1$ to $R^5$ below each represent a group large in the number of carbon atoms (for example: C4 to 8) or the compound represented by formula (2)) can easily provide a dispersion excellent in storage stability even at a lower concentration.

[Formula 3]

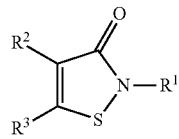

(1)

[Formula 4]

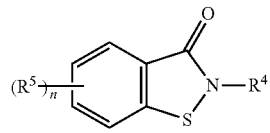

(2)

In formula (1), $R^1$ represents a hydrogen atom, or a substituted or unsubstituted hydrocarbon group, and $R^2$ and $R^3$ each independently represent a hydrogen atom, a halogen atom, or an organic group. Herein, $R^2$ and $R^3$ are optionally bound to each other to form a ring other than a benzene ring.

The organic group is preferably a substituted or unsubstituted hydrocarbon group.

The number of carbon atoms in the substituted or unsubstituted hydrocarbon group is preferably 1 to 12, more preferably 2 to 10, particularly preferably 4 to 8.

The unsubstituted hydrocarbon group in $R^1$ to $R^3$ may have a chain carbon backbone such as a linear or branched carbon backbone, or may have a cyclic carbon backbone. Specific examples of such a hydrocarbon group include a methyl group, an ethyl group, a propyl group, an isopropyl group, a butyl group, a hexyl group, a cyclohexyl group, an octyl group, and a 2-ethylhexyl group.

Examples of the substituted hydrocarbon group in $R^1$ to $R^3$ include a group where the hydrocarbon group is substituted with a substituent such as a halogen atom, an alkoxy group, a dialkylamino group, an acyl group, or an alkoxycarbonyl group.

The organic group in $R^2$ and $R^3$ may be an aliphatic hydrocarbon group such as an alkyl group or a cycloalkyl group, or may be an aromatic hydrocarbon group, and is preferably an aliphatic hydrocarbon group. The number of carbon atoms in the alkyl group is preferably 1 to 12, more preferably 1 to 10, particularly preferably 1 to 8. The aliphatic hydrocarbon group and the aromatic hydrocarbon group may have a substituent such as a halogen atom, an alkoxy group, a dialkylamino group, an acyl group, or an alkoxycarbonyl group.

Examples of the aliphatic hydrocarbon group include a methyl group, an ethyl group, a propyl group, an isopropyl group, a butyl group, a hexyl group, a cyclohexyl group, an octyl group, and a 2-ethylhexyl group.

$R^1$ preferably represents a hydrogen atom or an unsubstituted hydrocarbon group, more preferably represents a hydrocarbon group having 1 to 8 carbon atoms, $R^2$ preferably represents a hydrogen atom, and $R^3$ preferably represents a hydrogen atom or a halogen atom from the viewpoint that, for example, a compound more excellent in preservative/anti-bacterial effect is obtained, deterioration in the function of the magnetic particle by itself can be more suppressed, and a magnetic particle dispersion more excellent in storage stability can be easily obtained.

In particular, $R^1$ preferably represents a hydrocarbon group having 4 to 8 carbon atoms from the viewpoint that, for example, deterioration in the function of the magnetic particle by itself can be more suppressed.

In formula (2), $R^4$ represents a hydrogen atom, or a substituted or unsubstituted hydrocarbon group, $R^5$ independently represents a hydrogen atom, a halogen atom, or an organic group, and n represents an integer of 0 to 4.

Examples of the substituted or unsubstituted hydrocarbon group in $R^4$ include the same as in the substituted or unsubstituted hydrocarbon group in $R^1$ to $R^3$.

Examples of the organic group in $R^5$ include the same as in the organic group in $R^2$ and $R^3$.

$R^4$ preferably represents a hydrogen atom or an aliphatic hydrocarbon group, more preferably represents an alkyl group having 1 to 8 carbon atoms, and $R^5$ preferably represents a hydrogen atom from the viewpoint that, for example, a compound more excellent in preservative/anti-bacterial effect is obtained, deterioration in the function of the magnetic particle by itself can be more suppressed, and a magnetic particle dispersion more excellent in storage stability can be easily obtained.

Specific examples of the isothiazoline compound include 1,2-benzisothiazolin-3-one, 2-methyl-4,5-trimethylene-4-isothiazolin-3-one, 2-methyl-4-isothiazolin-3-one, 5-chloro-2-methyl-4-isothiazolin-3-one, 2-butyl-benzisothiazolin-3-one, 2-n-octyl-4-isothiazolin-3-one, and 4,5-dichloro-2-octyl-4-isothiazolin-3-one. In particular, the isothiazoline compound is preferably at least one selected from the group consisting of 2-methyl-4-isothiazolin-3-one, 2-n-octyl-4-isothiazolin-3-one, 5-chloro-2-methyl-4-isothiazolin-3-one, and 1,2-benzisothiazolin-3-one.

The content of the isothiazoline compound in the present dispersion based on 100 parts by mass of the magnetic particle is preferably 0.001 parts by mass or more, and preferably 10 parts by mass or less from the viewpoint that, for example, suppression of deterioration in the function of the magnetic particle by itself and the preservative/anti-bacterial effect are achieved in a well-balanced manner and a magnetic particle dispersion excellent in storage stability for a long period can be easily obtained, and is more preferably 0.002 parts by mass or more, particularly preferably 0.005 parts by mass or more, and more preferably 1 part by mass or less, further preferably 0.5 parts by mass or less, particularly preferably 0.1 parts by mass or less from the viewpoint that, for example, a dispersion more excellent in preservative/anti-bacterial effect is obtained.

<Aqueous Medium>

The present dispersion uses an aqueous medium, and thus can be particularly suitably used in, for example, biochemical applications, and is lower in the level of an adverse effect on the environment and is higher in safety for handling operators.

The aqueous medium is not particularly limited as long as the aqueous medium contains water, and may contain one or more non-aqueous media other than water.

The non-aqueous medium is not particularly limited as long as the non-aqueous medium is a solvent or has a composition so as to be miscible with water without forming any two layers. Specific examples of such a non-aqueous medium include alcohols such as methanol, ethanol, isopropyl alcohol, n-butyl alcohol, isobutyl alcohol, t-butyl alcohol, ethylene glycol, glycerin, propylene glycol, 2-ethyl-1-hexanol, 1-nonanol, and lauryl alcohol; and sulfoxide/sulfone compounds such as dimethylsulfoxide and sulfolane.

The content of the non-aqueous medium contained in the aqueous medium is preferably 10% by mass or less, more preferably 5% by mass or less, further preferably 2% by mass or less based on 100% by mass of the aqueous medium, and particularly preferably, the non-aqueous medium is not substantially contained. The phrase "not substantially contained" means that the non-aqueous medium is not purposely added to the present dispersion, and a non-aqueous medium inevitably incorporated in production of the present dispersion may be contained.

The content of the aqueous medium in the present dispersion is preferably 400 parts by mass or more, more preferably 900 parts by mass or more based on 100 parts by mass of the magnetic particle from the viewpoint that, for example, a magnetic particle dispersion excellent in storage stability for a long period can be easily obtained.

<Other Component(s)>

Not only the magnetic particle, the isothiazoline compound, and the aqueous medium, but also conventionally known additive (s) may be compounded in the present dispersion as long as the effects of the present invention are not impaired, and examples of such additive(s) include a surfactant, a dispersant, a pH adjuster, salts, and a stabilizer such as protein such as albumin and a high-molecular polymer.

Such additive (s) may be each used two or more kinds thereof.

<Physical Properties of Present Dispersion>

The pH of the present dispersion is not particularly limited, and is preferably 2 or more and preferably 13 or less from the viewpoint that, for example, the present dispersion can be suitably used in, for example, biochemical applications and aggregation of the magnetic particle can be easily suppressed, and is more preferably 4 or more, particularly preferably 6 or more, and more preferably 11 or less, particularly preferably 9 or less from the viewpoint that, for example, a magnetic particle dispersion more excellent in storage stability can be obtained.

In the case where a particle having a polar group or a structure that can be hydrolyzed on the surface thereof is used as the magnetic particle in the present dispersion, the reduction rate constant (reaction rate constant) of the amount of the polymer layer, the polar group, or the ligand is preferably low, and is preferably $3.0 \times 10^{-9}$ sec$^{-1}$ or less, more preferably $1.6 \times 10^{-9}$ sec$^{-1}$ or less.

<Application of Present Dispersion>

Applications of the present dispersion are not particularly limited, and the present dispersion is preferably used in biochemical applications, in particular, immunoassay. The present dispersion may be used as it is, and may be used with the magnetic particle being separated. In the latter case, the present dispersion may also be used after the magnetic particle is magnetically concentrated and the magnetic particle is separated from the dispersion and washed to wash off the isothiazoline compound once.

An immunological measurement method of a biological substance by use of the magnetic particle preferably includes a step of capturing a measurement object by the magnetic particle (hereinafter, also referred to as "reaction step"). The method preferably further includes a step of washing a reaction system including the magnetic particle, obtained in the reaction step, to perform B/F separation (hereinafter, also referred to as "washing step"), or a step of measuring the amount of the measurement object captured by the magnetic particle (hereinafter, referred also to as "measurement step").

(Reaction Step)

Suitable examples of the reaction step include a step of reacting the magnetic particle with the measurement object, thereby capturing the measurement object by the magnetic particle via a ligand immobilized on the magnetic particle, suitably, an antibody or an antigen to be specifically bound to the measurement object. In the reaction step, for example, an antibody labeled, which can be specifically bound to the measurement object, may coexist.

The reaction is usually performed at a pH of about 5 or more, preferably at a pH of about 6 or more, and usually at a pH of about 10 or less, preferably at a pH of about 8 or less, but not particularly limited. A buffer is usually used for maintaining an objective pH, and, for example, phosphoric acid or tris(hydroxymethyl)aminomethane is used.

The reaction may be performed, for example, at room temperature or more and 42° C. or less for about 5 minutes or more and about 60 minutes or less.

For example, a salt, protein such as albumin, and/or a surfactant can be, if necessary, added to the reaction system of the reaction.

A magnetic fluid treated with a polymer may also be used, and in such a case, the reaction may also be performed with the polymer being present.

In the case where the treatment of the magnetic particle with a polymer is performed in advance, a polymer solution and a solution containing the magnetic particle may be stirred in a proper container for about 1 minute or more, preferably about 2 minutes or more, and about 60 minutes or less, preferably about 10 minutes or less, and thereafter the magnetic particle may be recovered, and used in the reaction step.

(Washing Step)

The washing step includes performing B/F separation where the reaction system containing the magnetic particle capturing the measurement object is washed to remove an unreacted component and/or an unreacted labeled substance, after the reaction step.

Examples of the method of removing the unreacted substance from the magnetic particle by washing/separation preferably include a repeating method of repeating an operation where a magnetic field is allowed to act on a reaction container, to attach the magnetic particle to a reaction container wall for collection, thereafter a reaction supernatant is removed, a proper washing liquid (example: 0.01% Triton X 100-containing TBS (20 mM tris(hydroxymethyl)aminomethane, 0.9% NaCl, pH 7.4)) is, if necessary, further added, and a magnetic field is again allowed to act and then the supernatant is removed.

(Measurement Step)

The measurement step includes performing measurement of the measurement object captured by the magnetic particle, after the washing step. The measurement can be performed by a known immunoassay method, namely, for example, an enzyme immunoassay method (EIA), a radioimmunoassay method (RIA), or a fluoroimmunoassay method (FIA). For example, in the case where a labeled substance is a chemiluminescent substance or a fluorescent dye, the measurement of the measurement object can be made by measuring the luminescence or fluorescence emitted from the labeled substance, and in the case where a labeled substance is an enzyme, the measurement can be made by measuring the activity of the enzyme. In the case where a labeled substance is a radioisotope, the radioactivity of the labeled substance may be measured.

The measurement method may be any procedure of, for example, a sandwich method, a competition method, and a double-antibody method, and a sandwich method is preferably used in terms of, for example, sensitivity and specificity.

In measurement based on a sandwich method, a labeled antibody (secondary antibody) which can be specifically bound to the measurement object is added, and measurement is performed depending on the labeled form of the secondary antibody immobilized to the magnetic particle via the measurement object.

While the secondary antibody may be directly labeled with, for example, a radioisotope, an enzyme, biotin, a fluorescent substance, a chemiluminescent substance, gold colloid, latex, or a ferrite particle, the secondary antibody is preferably labeled with an enzyme from the viewpoint that safety is high and favorable measurement results can be expected. Examples of a suitable labeled enzyme include peroxidase, alkaline phosphatase, and galactosidase which are excellent in stability and where the enzyme activity is easily measured.

The secondary antibody bound can be detected or quantitatively determined according to any known method. For example, the secondary antibody by itself, labeled with, for example, an enzyme, luminant, or phosphor can also be directly detected or measured, or a tertiary antibody specific for the secondary antibody can be used and labeled in advance according to various methods, and labeling of the tertiary antibody can be detected or measured.

Examples of a suitable detection method include a method including reacting the secondary antibody labeled with an enzyme, with a substrate (luminescent substrate, fluorescence substrate, or chemiluminescent substrate) specific for the enzyme, to allow, for example, color-forming, fluorescence, or luminescence to be generated, and detecting the signal with measurement equipment, and a method where a chemiluminescent substrate that can allow for detection at high sensitivity is used is particularly preferable.

The reaction container for use in the above steps is preferably one that can be used through all the steps of immunoreaction without any exchange. Examples include a glass or plastic tube, a dedicated tray where a large number of tubes are integrally formed, a microtiter plate, and a reaction tube especially designed for a fully automatic EIA measuring apparatus, for repeated use with washing.

A substance to be measured in the immunological measurement method is, for example, a particular substance present in a biological specimen, and specific examples include protein, peptide, carbohydrate, and lipid. More specific examples can include virus-associated antigens or antibodies such as a HBs antigen and an anti-HBs antibody; bacterium-associated antigens or antibodies such as an anti-mycoplasma antibody, *Vibrio parahaemolyticus, Staphylococcus aureus, Legionella, campylobacter, Helicobacter pylori*, and MRSA; inflammatory markers such as C reactive protein (CRP) and a rheumatoid factor; tumor markers such as α-fetoprotein, CEA, CA19-9, and PSA; hormone; and allergy-associated antigens or antibodies such as allergen and an allergen-specific IgE antibody.

The biological specimen is not particularly limited, and examples include various body fluids such as serum, plasma, blood, and a spinal fluid, excretory substances such as urine, dilutions of feces, from which the solid content is removed, and various tissue extracts.

<Storage Method of Magnetic Particle Dispersion>

One embodiment of the present invention relates to a storage method of the magnetic particle dispersion, in which the aqueous medium, the magnetic particle, and the isothiazoline compound are mixed, preferably, the aqueous medium, the magnetic particle, and the isothiazoline compound are contacted.

Such three components can be mixed or contacted, to thereby easily provide a magnetic particle dispersion excellent in storage stability, and also easily provide a magnetic particle dispersion that not only is suppressed in deterioration in the function of the magnetic particle by itself, but also is excellent in preservative/bactericidal effect. Thus, deterioration in the function of the magnetic particle by itself can be suppressed, and therefore the method of mixing or contacting the three components can also be said to be the storage method of the magnetic particle.

The amount of each of the components in such a method may be comparable with the amount described above.

EXAMPLES

Hereinafter, the present invention will be described with reference to Examples in detail, but the present invention is not limited to such Examples.

Respective analysis conditions in Examples are as represented below.

<Measurement of Amount of Carboxyl Group on Surface>

The amount of the carboxyl group on the magnetic particle surface was measured using 794 Basic Titrino manufactured by Metrohm AG, according to an electrical conductivity measurement method.

<Measurement of Amount of Tosyl Group on Surface>

The amount of the tosyl group on the magnetic particle surface was determined by washing 100 mg of a surface-tosylated particle with 1 mL of pure water three times and then rotating and stirring it in 1 mL of 1.0 M ethanolamine for 24 hours, to thereby allow p-toluenesulfonic acid to be detached from the particle surface, removing the particle from the resulting solution, and thereafter measuring the absorbance at 261 nm (ε=331) in the resulting solution.

<Measurement of Amount of Protein G>

The amount of Protein G bound to the magnetic particle surface was calculated by measuring the amount of mouse IgG supplemented.

First, 200 μL of mouse IgG (40 μg/mL) dissolved in a 0.1 M TBS/0.01% Tween 20 aqueous solution (pH 7.4) was added to 2 mg of a Protein G-bound magnetic particle, and a reaction was allowed to run at room temperature for 30 minutes. After magnetic separation was conducted, the supernatant was removed, and the particle was washed with a TBS/0.01% Tween 20 aqueous solution (pH 7.4) three times. Thereafter, 200 μL of a 100 mM glycine buffer (pH 2.3) was added to elute the mouse IgG, the particle was removed from the resulting solution, and thereafter the absorbance at 280 nm in the resulting solution was measured to thereby calculate the amount of Protein G bound to the magnetic particle surface.

<Measurement of Amount of Oligo DNA>

The amount of Oligo DNA bound to the magnetic particle was quantitatively determined by reacting 500 μmol of Oligo DNA forming a complementary strand to the Oligo DNA labeled with fluorescein, with 3 mg of an Oligo DNA-bound magnetic particle in a light-shielding tube, stirring the resultant for 30 minutes, and thereafter measuring the amount of the fluorescence-labeled Oligo DNA remaining in the supernatant, with a fluorescence spectrophotometer (RF-6000 manufactured by Shimadzu Corporation, excitation at 490 nm, detection at 520 nm).

<Measurement of Amount of Mouse IgG>

The amount of Mouse IgG bound to the magnetic particle was measured according to a chemiluminescent enzyme immunoassay (CLEIA) method, specifically, the following method.

First, a Mouse IgG-bound magnetic particle was dissolved in a BSA-containing 50 mM TBS/0.01% Tween 20 aqueous solution (pH 7.5) to prepare a solution of 2% by mass of the magnetic particle, and 25 µL of the solution prepared was dispensed into each well of a 96-well white plate (manufactured by Corning Incorporated). Subsequently, 25 µL of a PSA antigen (0 to 25 ng/mL)-containing human serum or a standard solution, and furthermore 25 µL of an ALP (alkaline phosphatase)-labeled anti-PSA antibody liquid were sequentially dispensed, and reacted at 25° C. for 10 minutes. After the particle was separated by magnetic separation, the particle was washed with Tris buffer/0.01% Triton X-100 by use of a washer (Hydro Flex manufactured by Tecan Trading AG) for a 96-well plate, thereafter an ALP substrate solution (Lumipulse substrate solution manufactured by FUJIREBIO Inc.) was added to allow a reaction to run at 25° C. for 5 minutes, and the luminescence intensity was measured using a chemiluminescence measuring device (ARVO X5 manufactured by PerkinElmer Japan Co., Ltd.).

<Measurement of Amount of Streptavidin>

The amount of Streptavidin bound to the magnetic particle was quantitatively determined by reacting 2000 µmol of fluorescence-labeled biotin (Lucifer Yellow Cadaverin Biotin X, manufactured by Life Technology Inc.) with 1 mg of a Streptavidin-bound magnetic particle in a light-shielding tube, and thereafter measuring the amount of the fluorescence-labeled biotin remaining in the supernatant, with a fluorescence spectrophotometer (RF-6000 manufactured by Shimadzu Corporation, excitation at 440 nm, detection at 530 nm).

<Particle Size>

The volume average particle size of the particle was measured by a laser diffraction particle size distribution analyzer (manufactured by Shimadzu Corporation) SALD-200V.

<Parking Area>

The parking area was calculated using the following method. First, the volume average particle size of the particle, measured in the above method, and an average density of the particle, of 1.32 g/cm$^3$, were used to calculate the surface area per unit weight, and the surface area was divided by the amount of the polar group and the ligand, per unit weight of each particle, measured in the above method, thereby calculating the parking area.

<Viable Bacterial Count Test>

The viable bacterial count test was performed at n=3 by a membrane filter (MF) method using Milliflex (MXP-PLUSU01 manufactured by Merck Millipore S.A.S.).

First, BioBall SingleShot 30 *Staphylococcus aureus* (product number: 56045 manufactured by Sysmex bioMerieux Co., Ltd.) was added to 2 mL of a dispersion including 10% by mass of each magnetic particle produced in Examples and Comparative Examples, well stirred, and thereafter aspirated and filtered using a MF unit (product number: MSP000865 manufactured by Merck Millipore S.A.S.). After washing was performed using 10 mL of a phosphate buffer three times, MF was set up to an SCDA medium for milliflex (product number: MXSMCTS48 manufactured by Merck Millipore S.A.S.), and culturing was performed in an incubator set to 33° C. for 72 hours. The colony count in the medium was visually confirmed, and compared with the colony count in dissolution of BioBall in pure water.

[Production Example 1] Production of OH Group-Containing Magnetic Particle 1.1 Production of Nuclear Particle Two parts by mass of a 75% di(3,5,5-trimethylhexanoyl) peroxide solution ("Perloyl 355-75(S)" manufactured by NOF CORPORATION, hereinafter, referred to as "Perloyl") was mixed with 20 parts by mass of an aqueous 1% by mass sodium dodecyl sulfate solution, and the mixture was finely emulsified by an ultrasonic disperser. The resulting emulsified liquid was placed in a reactor in which 13 parts by mass of a polystyrene particle having a particle size of 0.77 µm and 41 parts by mass of water were placed, and stirred at 25° C. for 12 hours. After 95 parts by mass of methyl methacrylate (hereinafter, referred to as "MMA") and 5 parts by mass of trimethylolpropane trimethacrylate (hereinafter, referred to as "TMP") were emulsified in 400 parts by mass of an aqueous 0.1% sodium dodecyl sulfate solution in another container, the resulting emulsified liquid was placed in the reactor and stirred at 40° C. for 2 hours, and thereafter heated to 75° C. and subjected to polymerization for 8 hours. After cooling to room temperature, only the particle taken out by centrifugation was further washed with water, dried, and pulverized. The resultant was defined as a nuclear particle A-1. The particle size was 1.5 µm.

1.2 Production of Mother Particle (Formation of Magnetic Material Layer)

After acetone was added to an oily magnetic fluid (trade name: "EXP series" manufactured by Ferrotec Holdings Corporation) to precipitate a particle by sedimentation, and the particle was dried to thereby provide a ferrite superparamagnetic fine particle having a hydrophobized surface (average primary particle size: 0.02 µm).

Next, the nuclear particle A-1 (15 parts by mass) and 20 parts by mass of the superparamagnetic fine particle having a hydrophobized surface were well mixed in a mixer, and the mixture was treated using a hybridization systemModel NHS-0 (manufactured by NARA MACHINERY CO., LTD.) at a circumferential velocity of a blade (stirring blade) of 100 m/sec (16200 rpm) for 5 minutes, thereby providing a mother particle A-2 (particle size: 2.0 µm) having a magnetic material layer made of a superparamagnetic fine particle, on the surface thereof.

1.3 Formation of First and Second Polymer Layers on Mother Particle

A 1-L separable flask was charged with 333 parts by mass of an aqueous 0.5% by mass sodium dodecylbenzene sulfonate solution, and then with the mother particle A-2 (13.3 parts by mass), and the mixture was dispersed by a homogenizer and heated to 60° C. A pre-emulsion in which 18 parts by mass of MMA, 2 parts by mass of TMP, and 0.4 parts by mass of Perloyl were dispersed in 100 parts by mass of an aqueous 0.5% by mass sodium dodecylbenzene sulfonate solution placed in another container was dropped into the 1-L separable flask controlled at 60° C., over 2 hours, thereby forming a first polymer layer on the surface of the mother particle.

The 1-L separable flask after completion of the dropping was kept at 60° C. and stirring was conducted for 1 hour. Next, a pre-emulsion in which 8.75 parts by mass of glycidyl methacrylate, 1.25 parts by mass of TMP, and 0.2 parts by mass of Perloyl were dispersed in 50 parts by mass of an aqueous 0.5% by mass sodium dodecylbenzene sulfonate solution placed in another container was dropped into the 1-L separable flask controlled at 60° C., over one hour and 20 minutes. Thereafter, the temperature was raised to 75° C. and polymerization was continued for additional 2 hours to complete the reaction, thereby forming a second polymer layer on the first polymer layer.

Next, the particle in the separable flask was magnetically separated, and the particle was washed with distilled water. The above steps thus provided a magnetic particle A-3 (particle size: 3.0 μm) in which a second polymer layer having a glycidyl group was formed.

1.4 Hydrolysis of Glycidyl Group

Ten parts by mass of an aqueous 1% by mass sulfuric acid solution was added to the resulting magnetic particle A-3 (1.0 part by mass), and the particle was dispersed by ultrasonic irradiation for 5 minutes and then stirred at 60° C. for 5 hours. Subsequently, an operation where the magnetic particle was isolated from the resulting liquid by magnetic separation, dispersed in pure water, and magnetically separated and washed was repeated five times, thereby providing an OH group-containing magnetic particle A-4.

[Example 1] Carboxyl Group-Containing Magnetic Particle

After the magnetic particle A-4 (1.0 part by mass) was washed with 1,3-dioxolane three times, the particle was dispersed in 10 parts by mass of 1,3-dioxolane, a solution in which 1 part by mass of succinic anhydride and 0.15 parts by mass of triethylamine were dissolved was added thereto, and the resultant was stirred at 25° C. for 4 hours (introduction of carboxyl group). After completion of the reaction, the resulting particle was magnetically separated, and washed with 1,3-dioxolane three times and subsequently washed with distilled water four times, thereby providing a carboxyl group-containing magnetic particle (magnetic particle A-5). The resulting magnetic particle A-5 was dispersed in an aqueous 0.01% by mass 2-methyl-4-isothiazolin-3-one (hereinafter, referred to as "MIT") solution adjusted to a pH of 7.0 by use of ProClin 950 manufactured by Sigma-Aldrich, thereby preparing a dispersion containing 10% by mass of the magnetic particle A-5. The amount of the carboxyl group and the parking area of the particle were 10 μmol/g and 25.2 Å$^2$/carboxyl group, respectively.

The resulting dispersion was incubated in a constant-temperature bath at each of temperatures of 95° C., 75° C., and 50° C., the particle was partially taken out every certain period, and the amount of the carboxyl group on the surface was measured. The reaction rate (the reduction rate of the amount of the carboxyl group) constant k in incubation at each of the temperatures was calculated from the resulting value of the amount of the carboxyl group on the surface, thereby calculating the half-life $t_{1/2}$ (=ln2/k). Next, the calculated half-life at each of the temperatures was plotted against the reciprocal of each of the temperatures, thereby calculating the approximate curve representing the half-life at each of the temperatures, and thus the half-life (half-life at 4° C.) of the carboxyl group in storage at 4° C. was estimated. The results are shown in Table 1.

The calculated reaction rate constant k was used to calculate the time (time at 80%) at which the amount of the carboxyl group on the magnetic particle surface was 80% by mass of the initial value (the amount of the carboxyl group immediately after preparation of the magnetic particle A-5), and calculate the proportion (proportion after 2 years) of the amount of the remaining carboxyl group after 2 years of preparation of a magnetic particle A-5-containing dispersion relative to the initial value. The results are shown in Table 1.

The resulting dispersion was used to perform the viable bacterial count test, and it was thus confirmed that growth of microorganisms could be completely inhibited.

[Example 2] Carboxyl Group-Containing Magnetic Particle

The magnetic particle A-5 was dispersed in an aqueous 0.01% by mass MIT solution adjusted to a pH of 9.0, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test, and it was thus confirmed that growth of microorganisms could be completely inhibited.

[Example 3] Carboxyl Group-Containing Magnetic Particle

The magnetic particle A-5 was dispersed in an aqueous 0.01% by mass CMIT solution adjusted to a pH of 7.0 by use of 5-chloro-2-methyl-4-isothiazolin-3-one (hereinafter, referred to as "CMIT") manufactured by Sigma-Aldrich, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test, and it was thus confirmed that growth of microorganisms could be completely inhibited.

[Example 4] Carboxyl Group-Containing Magnetic Particle

The magnetic particle A-5 was dispersed in a mixed aqueous solution of 0.001% by mass of CMIT and MIT, adjusted to a pH of 7.0 by use of ProClin 300 manufactured by Sigma-Aldrich, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test, and it was thus confirmed that growth of microorganisms could be completely inhibited.

[Example 5] Carboxyl Group-Containing Magnetic Particle

The magnetic particle A-5 was dispersed in an aqueous 0.001% by mass BIT solution adjusted to a pH of 7.0 by use of 1,2-benzisothiazol-3(2H)-one (hereinafter, also referred to as "BIT") manufactured by Sigma-Aldrich, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test and no effect of suppressing growth of microorganisms was thus confirmed, but the BIT concentration was set to 0.05% by mass and it was thus confirmed that growth of microorganisms could be completely inhibited.

[Example 6] Carboxyl Group-Containing Magnetic Particle

The magnetic particle A-5 was dispersed in an aqueous 0.001% by mass OIT solution adjusted to a pH of 7.0 by use of 2-octyl-4-isothiazolin-3-one (hereinafter, referred to as "OIT") manufactured by Sigma-Aldrich, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test and it was thus confirmed that growth of microorganisms could be partially inhibited, and the OIT concentration was set to 0.01% by mass and it was thus confirmed that growth of microorganisms could be completely inhibited.

[Example 7] Carboxyl Group-Containing Magnetic Particle

The magnetic particle A-5 was dispersed in an aqueous 0.001% by mass BBIT solution adjusted to a pH of 7.0 by use of 2-butyl-1,2-benzisothiazol-3-one (hereinafter, also referred to as "BBIT") manufactured by BOC Sciences, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 1.

The resulting dispersion was used to perform the viable bacterial count test and no effect of suppressing growth of microorganisms was thus confirmed, but the BBIT concentration was set to 0.05% by mass and it was thus confirmed that growth of microorganisms could be completely inhibited.

[Example 8] Tosyl Group-Containing Magnetic Particle

The magnetic particle A-4 (1.0 part by mass) was washed with acetonitrile three time and then dispersed in 10 parts by mass of acetonitrile, 0.02 parts by mass of paratoluenesulfonyl chloride (manufactured by FUJIFILM Wako Pure Chemical Corporation) and 0.03 parts by mass of tributylamine were added thereto, and the resultant was stirred at 25° C. for 4 hours (introduction of tosyl group). After completion of the reaction, the resulting particle was magnetically separated, washed with acetonitrile three times and subsequently washed with distilled water four times, and then dispersed in an aqueous 0.001% by mass MIT solution adjusted to a pH of 7.0 by use of ProClin 950, thereby preparing a dispersion containing 10% by mass of a tosyl group-containing magnetic particle (magnetic particle A-6). The amount of the tosyl group and the parking area of the particle were 76 μmol/g and 3.3 Å$^2$/tosyl group, respectively.

The half-life at 4° C. (the half-life of the amount of the tosyl group in storage at 4° C.), the rate (the reduction rate of the amount of the tosyl group) constant k, the time at 80% (the time at which the amount of the tosyl group on the magnetic particle surface was 80% by mass relative to the initial value), and the proportion after 2 years (the proportion of the amount of the remaining tosyl group after 2 years of preparation of a magnetic particle A-6-containing dispersion relative to the initial value) were calculated in the same manner as in Example 1 except that the resulting dispersion was used. The results are shown in Table 1.

The resulting dispersion was used to perform the viable bacterial count test and it was thus confirmed that growth of microorganisms could be partially inhibited, and the MIT concentration was set to 0.01% by mass and it was thus confirmed that growth of microorganisms could be completely inhibited.

[Example 9] Protein G-Carried Magnetic Particle

The magnetic particle A-5 (1.0 part by mass) was washed with an aqueous 100 mM MES (2-Morpholinoethanesulfonic acid, monohydrate) solution (pH 5.0) twice. The solution after washing was subjected to magnetic separation to remove the supernatant, 10 parts by mass of an aqueous 100 mM MES solution (pH 5.0) and 0.03 parts by mass of Protein G were added, 0.1 parts by mass of EDC (1-ethyl-3-dimethylaminopropylcarbodiimide hydrochloride (manufactured by Dojindo Molecular Technologies, Inc.)) was further added, and the resultant was mixed by inverting at 25° C. for 15 hours. After completion of the reaction, the supernatant was removed by magnetic separation, and the residue was dispersed in a 0.01% by mass MIT-containing 50 mM Tris buffer/0.1% Tween 20 aqueous solution adjusted to a pH of 7.2 by use of ProClin 950, thereby preparing a dispersion containing 10% by mass of a Protein G-carried magnetic particle (magnetic particle A-7). The amount of the Protein G bound on the particle was 0.067 μmol/g.

The half-life at 4° C. (the half-life of the amount of the Protein G in storage at 4° C.), the rate (the reduction rate of the amount of the Protein G) constant k, the time at 80% (the time at which the amount of the Protein G on the magnetic particle surface was 80% by mass relative to the initial value), and the proportion after 2 years (the proportion of the amount of the remaining Protein G after 2 years of preparation of a magnetic particle A-7-containing dispersion relative to the initial value) were calculated in the same manner as in Example 1 except that the resulting dispersion was used and the incubation temperature was changed to 50° C., 37° C., and 25° C. The results are shown in Table 1.

The resulting dispersion was used to perform the viable bacterial count test, and it was thus confirmed that growth of microorganisms could be completely inhibited.

[Example 10] Oligo DNA-Carried Magnetic Particle

The magnetic particle A-5 (1.0 part by mass) was washed with an aqueous 100 mMMES solution (pH 5.5) twice. The solution after washing was subjected to magnetic separation to remove the supernatant, 10 parts by mass of an aqueous 100 mM MES solution (pH 5.5) and 0.025 parts by mass of Oligo DNA were added, 0.12 parts by mass of EDC (manufactured by Dojindo Molecular Technologies, Inc.) was further added, and the resultant was mixed by inverting at 50° C. for 18 hours. After completion of the reaction, the supernatant was removed by magnetic separation, and the residue was dispersed in a 0.01% by mass MIT-containing 50 mM Tris buffer/0.1% Tween 20 aqueous solution adjusted to a pH of 7.2 by use of ProClin 950, thereby preparing a dispersion containing 10% by mass of an Oligo DNA-carried magnetic particle (magnetic particle A-8). The amount of the Oligo DNA bound on the particle was 0.13 µmol/g.

The half-life at 4° C. (the half-life of the amount of the Oligo DNA in storage at 4° C.), the rate (the reduction rate of the amount of the Oligo DNA) constant k, the time at 80% (the time at which the amount of the Oligo DNA on the magnetic particle surface was 80% by mass relative to the initial value), and the proportion after 2 years (the proportion of the amount of the remaining Oligo DNA after 2 years of preparation of a magnetic particle A-8-containing dispersion relative to the initial value) were calculated in the same manner as in Example 1 except that the resulting dispersion was used and the incubation temperature was changed to 80° C., 60° C., and 40° C. The results are shown in Table 1.

The resulting dispersion was used to perform the viable bacterial count test, and it was thus confirmed that growth of microorganisms could be completely inhibited.

[Example 11] Mouse IgG-Carried Magnetic Particle

The magnetic particle A-5 (1.0 part by mass) was washed with an aqueous 100 mMMES solution (pH 5.0) twice. The solution after washing was subjected to magnetic separation to remove the supernatant, 10 parts by mass of an aqueous 100 mM MES solution (pH 5.0) and 0.01 parts by mass of a Mouse IgG solution (anti-PSA antibody, clone name C157) were added, 0.1 parts by mass of EDC (manufactured by Dojindo Molecular Technologies, Inc.) was further added, and the resultant was mixed by inverting at 25° C. for 1 hour. After completion of the reaction, the supernatant was removed by magnetic separation, and the residue was dispersed in a 0.01% by mass MIT-containing 50 mM Tris buffer/0.1% Tween 20 aqueous solution adjusted to a pH of 7.2 by use of ProClin 950, thereby preparing a dispersion containing 10% by mass of a Mouse IgG-carried magnetic particle (magnetic particle A-9). The amount of the Mouse IgG bound in the particle was 0.053 µmol/g.

The half-life at 4° C. (the half-life of the amount of the Mouse IgG in storage at 4° C.), the rate (the reduction rate of the amount of the Mouse IgG) constant k, the time at 80% (the time at which the amount of the Mouse IgG on the magnetic particle surface was 80% by mass relative to the initial value), and the proportion after 2 years (the proportion of the amount of the remaining Mouse IgG after 2 years of preparation of a magnetic particle A-9-containing dispersion relative to the initial value) were calculated in the same manner as in Example 1 except that the resulting dispersion was used and the incubation temperature was changed to 50° C., 37° C., and 25° C. The results are shown in Table 1.

The resulting dispersion was used to perform the viable bacterial count test, and it was thus confirmed that growth of microorganisms could be completely inhibited.

[Example 12] Streptavidin-Carried Magnetic Particle

The magnetic particle A-5 (1.0 part by mass) was washed with an aqueous 100 mM MES solution (pH 5.0) twice. The solution after washing was subjected to magnetic separation to remove the supernatant, 20 parts by mass of an aqueous 100 mM MES solution (pH 5.0) and 0.02 parts by mass of a Streptavidin solution (manufactured by Roche Diagnostics K.K., Streptavidin, reconbinat) were added, 0.02 parts by mass of EDC (manufactured by Dojindo Molecular Technologies, Inc.) was further added, and the resultant was mixed by inverting at 25° C. for 1 hour. After completion of the reaction, the supernatant was removed by magnetic separation, and the residue was dispersed in a 0.01% by mass MIT-containing 50 mM Tris buffer/0.1% Tween 20 aqueous solution adjusted to a pH of 7.5 by use of ProClin 950, thereby preparing a dispersion containing 10% by mass of a Streptavidin-carried magnetic particle (magnetic particle A-10). The amount of the Streptavidin bound on the particle was 0.1375 µmol/g.

The half-life at 4° C. (the half-life of the amount of the Streptavidin in storage at 4° C.), the rate (the reduction rate of the amount of the Streptavidin) constant k, the time at 80% (the time at which the amount of the Streptavidin on the magnetic particle surface was 80% by mass relative to the initial value), and the proportion after 2 years (the proportion of the amount of the remaining Streptavidin after 2 years of preparation of a magnetic particle A-10-containing dispersion relative to the initial value) were calculated in the same manner as in Example 11 except that the resulting dispersion was used. The results are shown in Table 1.

The resulting dispersion was used to perform the viable bacterial count test, and it was thus confirmed that growth of microorganisms could be completely inhibited.

[Comparative Example 1] Carboxyl Group-Containing Magnetic Particle

The carboxyl group-containing magnetic particle A-5 was dispersed in an aqueous 0.09% by mass sodium azide (manufactured by FUJIFILM Wako Pure Chemical Corporation) solution adjusted to a pH of 7.0, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 2.

The resulting dispersion was used to perform the viable bacterial count test, and it was thus confirmed that growth of microorganisms could be completely inhibited.

[Comparative Example 2] Carboxyl Group-Containing Magnetic Particle

The carboxyl group-containing magnetic particle A-5 was dispersed in an aqueous 0.09% by mass sodium azide (manufactured by FUJIFILM Wako Pure Chemical Corporation) solution adjusted to a pH of 9.0, thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 2.

The resulting dispersion was used to perform the viable bacterial count test, and it was thus confirmed that growth of microorganisms could be completely inhibited.

[Comparative Example 3] Carboxyl Group-Containing Magnetic Particle

The carboxyl group-containing magnetic particle A-5 was dispersed in pure water (pH 7.0), thereby preparing a dispersion containing 10% by mass of the magnetic particle.

The half-life at 4° C., the rate constant k, the time at 80%, and the proportion after 2 years were calculated in the same manner as in Example 1 except that the resulting dispersion was used. The results are shown in Table 2.

The resulting dispersion was used to perform the viable bacterial count test and no effect of suppressing growth of microorganisms was thus confirmed.

[Comparative Example 4] Tosyl Group-Containing Magnetic Particle

The tosyl group-containing magnetic particle A-6 was dispersed in an aqueous 0.09% by mass sodium azide (manufactured by FUJIFILM Wako Pure Chemical Corporation) solution adjusted to a pH of 7.0, thereby preparing a dispersion containing 10% by mass of the magnetic particle.

The half-life at 4° C., the rate constant k, the time at 80%, and the proportion after 2 years were calculated in the same manner as in Example 8 except that the resulting dispersion was used. The results are shown in Table 2.

The resulting dispersion was used to perform the viable bacterial count test, and it was thus confirmed that growth of microorganisms could be completely inhibited.

[Comparative Example 5] Protein G-Carried Magnetic Particle

The Protein G-carried magnetic particle A-7 was dispersed in a 0.09% by mass sodium azide-containing 50 mM Tris buffer/0.1% Tween 20 aqueous solution adjusted to pH of 7.2, thereby preparing a dispersion containing 10% by mass of the magnetic particle.

The half-life at 4° C., the rate constant k, the time at 80%, and the proportion after 2 years were calculated in the same manner as in Example 9 except that the resulting dispersion was used. The results are shown in Table 2.

The resulting dispersion was used to perform the viable bacterial count test, and it was thus confirmed that growth of microorganisms could be completely inhibited.

[Comparative Example 6] Oligo DNA-Carried Magnetic Particle

The Oligo DNA-carried magnetic particle A-8 was dispersed in a 0.09% by mass sodium azide-containing 50 mM Tris buffer/0.1% Tween 20 aqueous solution adjusted to pH of 7.2, thereby preparing a dispersion containing 10% by mass of the magnetic particle.

The half-life at 4° C., the rate constant k, the time at 80%, and the proportion after 2 years were calculated in the same manner as in Example 10 except that the resulting dispersion was used. The results are shown in Table 2.

The resulting dispersion was used to perform the viable bacterial count test, and it was thus confirmed that growth of microorganisms could be completely inhibited.

[Comparative Example 7] Mouse IgG-Carried Magnetic Particle

The Mouse IgG-carried magnetic particle A-9 was dispersed in a 0.09% by mass sodium azide-containing 50 mM Tris buffer/0.1% Tween 20 aqueous solution adjusted to pH of 7.2, thereby preparing a dispersion containing 10% by mass of the magnetic particle.

The half-life at 4° C., the rate constant k, the time at 80%, and the proportion after 2 years were calculated in the same manner as in Example 11 except that the resulting dispersion was used. The results are shown in Table 2.

The resulting dispersion was used to perform the viable bacterial count test, and it was thus confirmed that growth of microorganisms could be completely inhibited.

[Comparative Example 8] Streptavidin-Carried Magnetic Particle

The Streptavidin-carried magnetic particle A-10 was dispersed in a 0.09% by mass sodium azide-containing 50 mM Tris buffer/0.1% Tween 20 aqueous solution adjusted to a pH of 7.5, thereby preparing a dispersion containing 10% by mass of the magnetic particle.

The half-life at 4° C., the rate constant k, the time at 80%, and the proportion after 2 years were calculated in the same manner as in Example 12 except that the resulting dispersion was used. The results are shown in Table 2.

The resulting dispersion was used to perform the viable bacterial count test, and it was thus confirmed that growth of microorganisms could be completely inhibited.

TABLE 1

|  | Example 1 | Example 2 | Example 3 | Example 4 | Example 5 | Example 6 | Example 7 |
|---|---|---|---|---|---|---|---|
| Particle modification | COOH group | COOH group | COOH group | COOH group | COOH group | COOH group | COOH group |
| Additive | MIT | MIT | CMIT | CMIT/MIT | BIT | OIT | BBIT |
| Additive concentration (ppm) | 100 | 100 | 100 | 10 | 10 | 10 | 10 |
| Surfactant | None | None | None | None | None | None | None |
| Parking area (Å$^2$) | 25.2 | 25.2 | 25.2 | 25.2 | 25.2 | 25.2 | 25.2 |
| pH | 7.0 | 9.0 | 7.0 | 7.0 | 7.0 | 7.0 | 7.0 |
| Half-life at 4° C. (year) | 13.1 | 12.8 | 13.8 | 11.2 | 13.4 | 16.3 | 18 |
| Rate constant k (sec$^{-1}$) | 1.68.E−09 | 1.72.E−09 | 1.59.E−09 | 1.96.E−09 | 1.64.E−09 | 1.35.E−09 | 1.22.E−09 |
| Time at 80% (year) | 4.2 | 4.1 | 4.4 | 3.6 | 4.3 | 5.2 | 5.8 |
| Proportion after 2 years (%) | 90.0 | 89.7 | 90.4 | 88.4 | 90.2 | 91.8 | 92.6 |

TABLE 1-continued

|  | Example 8 | Example 9 | Example 10 | Example 11 | Example 12 |
|---|---|---|---|---|---|
| Particle modification | Tosyl group | Protein G | Oligo DNA | Mouse IgG | Streptavidin |
| Additive | MIT | MIT | MIT | MIT | MIT |
| Additive concentration (ppm) | 10 | 100 | 100 | 100 | 100 |
| Surfactant | None | Tween 20 | Tween 20 | Tween 20 | Tween 20 |
| Parking area ($Å^2$) | 3.3 | 25.2 | 25.2 | 25.2 | 25.2 |
| pH | 7.0 | 7.2 | 7.2 | 7.2 | 7.5 |
| Half-life at 4° C. (year) | 11.8 | 17.9 | 14.3 | 15.8 | 23.2 |
| Rate constant k ($sec^{-1}$) | 1.86.E−09 | 1.23.E−09 | 1.54.E−09 | 1.39.E−09 | 9.47.E−10 |
| Time at 80% (year) | 3.8 | 5.8 | 4.6 | 5.1 | 7.5 |
| Proportion after 2 years (%) | 88.9 | 92.5 | 90.8 | 91.6 | 94.2 |

TABLE 2

|  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Particle modification | COOH group | COOH group | COOH group | Tosyl group | Protein G | Oligo DNA | Mouse IgG | Streptavidin |
| Additive | $NaN_3$ | $NaN_3$ | None | $NaN_3$ | $NaN_3$ | $NaN_3$ | $NaN_3$ | $NaN_3$ |
| Additive concentration (ppm) | 900 | 900 | — | 900 | 900 | 900 | 900 | 900 |
| Surfactant | None | None | None | None | Tween 20 | Tween 20 | Tween 20 | Tween 20 |
| Parking area ($Å^2$) | 25.2 | 25.2 | 25.2 | 3.3 | 25.2 | 25.2 | 25.2 | 25.2 |
| pH | 7 | 9 | 7 | 7 | 7.2 | 7.2 | 7.2 | 7.5 |
| Half-life at 4° C. (year) | 5.6 | 3.1 | 7 | 5.2 | 8.7 | 9.6 | 9.3 | 10.3 |
| Rate constant k ($sec^{-1}$) | 3.92.E−09 | 7.09.E−09 | 3.14.E−09 | 4.23.E−09 | 2.53.E−09 | 2.29.E−09 | 2.36.E−09 | 2.13.E−09 |
| Time at 80% (year) | 1.8 | 1.0 | 2.3 | 1.7 | 2.8 | 3.1 | 3.0 | 3.3 |
| Proportion after 2 years (%) | 78.1 | 63.9 | 82.0 | 76.6 | 85.3 | 86.6 | 86.2 | 87.4 |

It was confirmed from a series of Examples that an isothiazoline compound was used to exert the effect of enhancing storage stability of a magnetic particle (dispersion), regardless of the type of the magnetic particle. It was confirmed that an isothiazoline compound higher in hydrophobicity allowed the effect of enhancing storage stability of a magnetic particle (dispersion) to be exerted even in the case where the compound was contained at a low concentration. It is presumed that the interaction with a polymer on the magnetic particle and/or a functional group on the surface is involved.

It was also confirmed that an isothiazoline compound used at a proper concentration could impart not only an enhancement in storage stability of a magnetic particle (dispersion), but also a high preservative effect.

On the other hand, it was confirmed that sodium azide being a common preservative agent, used in Comparative Example, allowed a preservative effect to be exerted, but resulted in deterioration in storage stability of a magnetic particle (dispersion), regardless of the pH of a magnetic particle dispersion.

The invention claimed is:

1. A magnetic particle dispersion, comprising:
a magnetic particle,
an isothiazoline compound in an amount of 0.001 to 1 part by mass based on 100 parts by mass of the magnetic particle, and
an aqueous medium,
wherein the isothiazoline compound is a compound of formula (1):

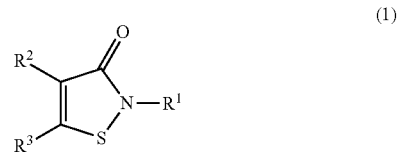

wherein $R^1$ represents a hydrogen atom, or a linear or branched chain hydrocarbon group having 1 to 8 carbon atoms, and $R^2$ and $R^3$ each independently represent a hydrogen atom, a halogen atom, or an aliphatic hydrocarbon group having 1 to 12 carbon atoms, in which $R^2$ and $R^3$ are optionally bound to each other to form a ring other than a benzene ring, and wherein the magnetic particle has a first polymer layer having hydrophobicity on the surface of a mother particle and which has a second polymer layer having a glycidyl group, or at least one polar group selected from an amino group, an aldehyde group, a carboxyl group, a tosyl group, a mercapto group, a hydroxyl group, an epoxy group, and an active ester group on at least the surface of the magnetic particle, on the first polymer layer.

2. The magnetic particle dispersion according to claim 1, wherein when the magnetic particle has a polar group or a ligand, a content of the polar group or the ligand in the magnetic particle is from 0.1 to 100 µmol/g.

3. The magnetic particle dispersion according to claim 1, wherein when the magnetic particle has a polar group, a parking area of the polar group in the magnetic particle is 2.5 ($Å^2$/polar group and ligand) or more.

4. The magnetic particle dispersion according to claim 1, wherein the magnetic particle has a structure that is optionally hydrolyzed.

5. The magnetic particle dispersion according to claim 1, wherein a volume average particle size of the magnetic particle is from 0.1 to 10 µm.

* * * * *